United States Patent
Xu et al.

(10) Patent No.: US 9,944,962 B2
(45) Date of Patent: Apr. 17, 2018

(54) CLONE OF XIAMENMYCIN BIOSYNTHESIS GENE CLUSTER AND HETEROLOGOUS EXPRESSION THEREOF

(71) Applicant: SHANGHAI JIAO TONG UNIVERSITY, Shanghai (CN)

(72) Inventors: Jun Xu, Shanghai (CN); Yong Yang, Shanghai (CN); Ling Fu, Shanghai (CN); Minjuan Xu, Shanghai (CN); Zhongyuan You, Shanghai (CN)

(73) Assignee: SHANGHAI JIAO TONG UNIVERSITY, Shanghai (CN)

( * ) Notice: Subject to any disclaimer, the term of this patent is extended or adjusted under 35 U.S.C. 154(b) by 0 days.

(21) Appl. No.: 14/902,342

(22) PCT Filed: Apr. 21, 2014

(86) PCT No.: PCT/CN2014/075784
§ 371 (c)(1),
(2) Date: Dec. 31, 2015

(87) PCT Pub. No.: WO2015/000327
PCT Pub. Date: Jan. 8, 2015

(65) Prior Publication Data
US 2016/0222422 A1 Aug. 4, 2016

(30) Foreign Application Priority Data
Jul. 1, 2013 (CN) .......................... 2013 1 0273055

(51) Int. Cl.
*C12P 17/06* (2006.01)
*C12N 15/52* (2006.01)
*C12R 1/465* (2006.01)

(52) U.S. Cl.
CPC .............. *C12P 17/06* (2013.01); *C12N 15/52* (2013.01); *C12R 1/465* (2013.01)

(58) Field of Classification Search
None
See application file for complete search history.

(56) References Cited

PUBLICATIONS

You et al. Mar Drugs. Oct. 22, 2013;11(10):4035-49.*
Min-Juan Xu et al. Identification and Characterization of an Anti-Fibrotic Benzopyran Compound Isolated from Mangrove-Derived Streptomyces xiamenensis. Marine Drugs. 2012, 10, 639-654, ISSN 1660-3397.
Zhong-Yuan You et al. Identification of Two Novel Anti-Fibrotic Benzopyran Compounds Produced by Engineered Strains Derived from Streptomyces xiamenensis M1-94P that Originated from Deep-Sea Sediments. Marine Drugs 2013, 11, 4035-4049, ISSN 1660-3397.
Xiao-Jin Liu et al, Xiamenmycin Attenuates Hypertrophic Scars by Suppressing Local Inflammation and the Effects of Mechanical Stress. Journal of Investigative Dermatology, Jan. 10, 2013; p. 1-10.

* cited by examiner

*Primary Examiner* — Christian Fronda

(57) ABSTRACT

The present invention involves the application of a gene cluster, and bacterial strains that used in the biosynthesis of Xiamenmycin. The nucleotide sequence of the gene cluster is showed as SEQ ID NO.1, with the whole length of 5189 base pairs. The present invention involves *Streptomyces xiamenensis* CGMCC No. 5670 and its mutant strain, and the method that how the mentioned bacterial strain produces Xiamenmycin. The present invention provides the strain sources by using *Streptomyces xiamenensis*, its mutant strains or genetically engineered microbial strains carrying the above-mentioned Xiamenmycin biosynthesis gene cluster for cultivation and produce benzopyran compound Xiamenmycin through biosynthesis. The mutant strains can be used in industrial production.

1 Claim, 5 Drawing Sheets

Xiamenmycin B, 3

(A)

(B)

SEQUENCE LISTING

<160> NUMBER OF SEQ ID NOS: 28

<210> SEQ ID NO 1
<211> LENGTH: 5189
<212> TYPE: DNA
<213> ORGANISM: Streptomyces Xiamenesis

<400> SEQUENCE: 1

```
atgagacagg agcatcgggt ggacataccc gagaacttga cgcgccgttg ggcggagcat      60
gcgcgcgaga aggggtggag cgaacggacc gcgttccatg ccgacggccg ggcgtggacc     120
ttcgcggagg tgttcgacgg ggcggcgagg gtggcggccg gataccggtc gcacggtcta     180
cgcaccggtg accgggtgct gctcgccttg cccgacagtg tggagatggt ctggtgtctg     240
ctcggcgcgt ggcaggcggg tctcgtcgcg gtgccggtga acgtccagat gagccggatg     300
gatctgacgc gcgacgtggt cacggctgaa ccggcgcttg tcgtggtcga cccggagacc     360
gccgggtggc tcggggacag cgggccggct cccaccaccg aggtcgttcc gctcgtggct     420
gcagagccgg aggaggcatt cgccacgggc gggaacgccg ccgcgctggc tgtgttcacc     480
tccggcacca ccggggcgcc gaagttgtgc ttcttccgcc accgcgacct cggcgcccca     540
cgcgcgcctg gcctggtgag cggacccgac accgtcgggc tctcggtgtc gcgcatgtac     600
ttcgtgggcg ggctgagcgc gtcggtgttc accaccctcg aaaccgggca ggtggccgtg     660
ctgtcgcggc cccgcgcgac cccggccgcc gcggtcgagc tcatgcggcg ccacaacgtc     720
accgtcctgt tcgcgcagcc gagcttcctg gcgcggctgc tgctcgaacc cggccatgcc     780
gaggtactgg gtaacgtccg tcaggccttc tgcgccgggg aagtgttcac cgcgcgactg     840
cgcgagcagc tggtcccgat catgggcccc cggctgctca acacctacgg aacgacggaa     900
gccggtgccg tcgcagtcgg cccgcccgcg gtctacgacg tgccgtcggc ggtcggtccg     960
```

```
cccctgcccg gcaggccggt gcgtgtcgtc gacgccgacg gacacgagct gcccacgggc      1020
agcatgggcg agctgcacat ccgcgtcccc atcgccaccc gcggcgtcgc ccacggcagc      1080
ctcggacccg acatcctgac cgacgtgtgg tggccgaccg gcgacctcgc ctccatcgac      1140
gagaacggtg ttgtgcacgc gcatggccgg ctcgacgaca tcgaggtgat cggcggacag      1200
aacctggtgc cgagcgaggt cgaacgcctg ctggagagcc acccgcgcgt gctggaggcg      1260
gcggtcagct ccgtgtggcg cccggccggg gacacgagcc tgcgcgccta cgtcgtcgcc      1320
gccgcggcac ccggctcgtc cgacgaaggg ccggtgcggg gtgacgacgc gctcgccgcc      1380
gaattggtcg agctcgcccg atccaccctg tcctggtaca aggttccgca ggacgtcgta      1440
tggctggaca cactgccccg caacggcaac ggcaaattgc tgcgcagggt actccgcgca      1500
cagggcgacg agttcatcca gccccatcgt cactatccgg cgtcgaatgc gcctcgaacg      1560
tgaacacggt tcggcaaaca ccgttaggac aaggcggcgt tgacgcaacg cttactgcg      1620 ccgccaacga atcgatggcc catcaggaag acaccacagc cgacaaattg aggataacgg      1680
gacgagatcg gcgcggcgcg aacaaacgtg tccgagatca cggggaaacc gtgttagccg      1740
aggtgggctt tctgcaagag tcacaacaat aaccctcgcc cggtcaggtg atcgatattt      1800
ccgctcaacc ctcgcagcag agcacgcgat atcggttcgt cgtgccgagc atcgcggcgt      1860
cggtcgtgcc gagtgcgccg aaggccgtcc tcccctatct acaactgcg cgtatgcacg      1920 cgcccatagg cagttggctg tacctcctcc ccggcctgtg ggggatcgcg ctcgcctcgg      1980
cggggctgcc cgactggcgc caggtgctgc tgttcacggt cggtggggtg ctggtgcgcg      2040
gcttcggctg cgtcgtcaac gaccttgccg accgcaagtt cgacgcccgg gtggcacgta      2100
ccgtcgggag gccgctcgtg gccggtacgg tcacggtcac gggagcgctt gtcttcgccg      2160
tggtgcaggc ggtggcgggg ctgctcgtgc tggctgcggc cagcgttccg gcggcggtgt      2220
tcgtggccgc ctcctatccg ctcgtggtcg cgtacccgtt catgaagcgg atcacctact      2280
ggccgcaggc ctggctgggg atggtcttcg gctgctacat cctcgcgggt tggctcgcgg      2340
tggccgggag gatcgagact cccgcgctcc tgctcttcgt cgccggtgtc ttctggacgc      2400
tggggtacga cacgatctac gcccaccagg acaaggcgga cgacgtgcag gtgggggtga      2460
agtccctcgc gctgcgcctc ggcagggcga cccggccctg ggtcgccggg ttttacgggg      2520
cgaccgtggt cgggatcgtg gctgccggag ccgtcgccga tctgcactgg acgttctacg      2580
cgctgtttct gccgggcgtg gcacacctgc tctggcaggt ggtgacggtg gacatcgaca      2640
gccctgccga ctgccgggaa aagttcatgg caaaccgttt cttcgggtgg ctcgtgctcg      2700
tcgccatcgt tgcggggaga gtcttttgag gcgcggccac gcggtcgcac cggagcgacg      2760
gcggaggaga tacatgtatg caggcccctg gtccgtgcgc acgagtcgc gcagcctggc      2820 ccagttcgtg gcgctcttgc gggagccggc gagtttggcc accgaggtgc tggaggagtg      2880
gtgcggtgct ccggtcaccg cggagatccg ccaccgcgcg gatggccaat tactcgtccc      2940
gccggctgag cggacattcg gcgggggttc ggcgcaggcg gagcgagccc ccttcttacc      3000
gccggagcgg gtggccgaac tgatgcggct ctcgacgggt gcccgtgtgc agttccgcac      3060
cgtttacctg cgccgccgga ccgaaaaggt cgtcaccgcg ggcgccgtcg tggcgctcga      3120
gcgcataagc cccgaggaac acgccgtgct cagcaccacc aacgcaccgc tggggccggt      3180 gctgccgcg ggcggtggag tgcggcgcgt gatggtcacg tccgaaccga cccgcctcga      3240
ccccgccgtg cgaccgccct gcgacgccga cgctcccgtg ctgaccgtca ccgcgctgct      3300
```

-continued

```
gtgtcgtgga accatgcccg tcggcctcgt gcgggaggct ttcctgccgt gtctcctcga    3360
tcgagacgcc gtccacgacg catgagggat cccatgccga actctcccgc cgcggtcttc    3420
gagcggctca ccaccaccgt cccgccggtc cgcatcgagg ttcgtctcgg caccgcctgc    3480
gtgctcggcg gcggcgtcgc cggcctggtc gcggcccgcg tactcgcgga ccacgccaac    3540
cgtgtcgtga tcatcgagcc cgacctgccg gaagccgcgc tcagcggcgc ggctcgtccc    3600
ggcgtcccgc agggctccca ggtgcacctc ctgctgcccg gcggacgcgc gcagctcgaa    3660
cgcttcttcc ccggtgtcgt ggcagaggcc ctcgccgggg gtgctgtgtc gtgcggtccg    3720
gagcgcaccg ccacctacct cgacgacatc gagcagatcg ccacgcccaa cgcgcggttc    3780
ctggggagca gtcgccccctt cctggagacg ctgatccgtc ggcgcgcgct cgcactgccc    3840
aacgtcgagc tggtgagtgg acgcgtcatt gggctgcggt acgcgcgcgg cgccgtcgag    3900
tcggtgcgct acgcggttgg cggcgaccac gtcgtcgccc cagccgactt cgtcgtcgac    3960
gcctccggcc gcggcagcag gctgagtgac tggctggagc agggcggctg gccccgaccg    4020
gagacgcaac ggctccagac cgacatccgc tacttgtctg cccgtttcac gcgctcggcc    4080
gactgggacg gcccccctcag cggcatctcc cgctacagcc cgcatttccc gaaggacatc    4140
gccggagcgg cggtcaaccc gatcgagaac caacagtggg tggtgatgct cgcccacttc    4200
ggcaacggcg ccgagggccg cacggccgac gagttcgtcg cccggtgccg tgagctgcca    4260
ccgatcttcc aggaagccgt caagggcgaa atcgtcggcg aggttgtccc gtaccgccac    4320
cccgacagca ggtggcgcca cttcgaggcg ctcgaccgct tccccgcccg cctggcggtc    4380
ctcggcgacg ccgtcgcctc gttcaacccc ctgtacgggc aaggtatgtc ctcggccgcg    4440
ctccacgcct cctgcctgtc ggagttcctg cgctctggcc ccgacctgga cgccccggcc    4500
cggcacttcc tcgagctgga aaaggtcgtc gtcgaagccg cgtggcagac gtccacggcc    4560
ggcgacgcca tccggctggg cctggcaacg ccaccggcca ccgatcaggg gcggcggcag    4620
gcgtgggccc tgccgacaggt acgggaggca gcgggccggg acgagcaggt cggcacggcc    4680
ctgcgggcgg tggggttcat gaccgcccat ccggcgtcgc tgatggcacc ggatttggtg    4740
cttcgcgcgc gcgggtcaa tggtgtgccg gaggagcgga tccggcagga gtacacgatg    4800
atggagacga cgtgatgggc cagacgacgc acacagcact cgaccgctac atggagctcg    4860
ccgaccgcgc cgtgcgggac ccctcggcgc tggcggagct ccccacgatc ttcgcgcccg    4920
acgccaccgt gacgctgcgc gacgagccgg tgaccggcat gcccgccatc atggagttct    4980
accgggtgtt cgtggcggcg gtggccgaga gcaagcacta ctggacaacc acgatcctcg    5040
aggacggcac gatcgagtcg cactgggtcg tcgcggcgcg ccgggccgac ggcagcctga    5100
tgaccgcagc cggggtcgag cacgcgaccg tcgacaccga tgggttgatc acgaacctgc    5160
gcaaccggta cacccgtacg ccgggctga                                      5189
```

<210> SEQ ID NO 2
<211> LENGTH: 19
<212> TYPE: DNA
<213> ORGANISM: Artificial Sequence
<220> FEATURE:
<223> OTHER INFORMATION: forward

<400> SEQUENCE: 2
tggctgggga tggtcttcg                                                    19

<210> SEQ ID NO 3
<211> LENGTH: 19

<212> TYPE: DNA
<213> ORGANISM: Artificial Sequence
<220> FEATURE:
<223> OTHER INFORMATION: reverse

<400> SEQUENCE: 3
ccttgtcctg gtgggcgta                                          19

<210> SEQ ID NO 4
<211> LENGTH: 35
<212> TYPE: DNA
<213> ORGANISM: Artificial Sequence
<220> FEATURE:
<223> OTHER INFORMATION: forward primer

<400> SEQUENCE: 4
gctctagacg gctggagtgt agcgagtctg gaatg                        35

<210> SEQ ID NO 5
<211> LENGTH: 29
<212> TYPE: DNA
<213> ORGANISM: Artificial Sequence
<220> FEATURE:
<223> OTHER INFORMATION: reverse primer

<400> SEQUENCE: 5
ggaattcccc ggacgtggga gcgataggg                               29

<210> SEQ ID NO 6
<211> LENGTH: 60
<212> TYPE: DNA
<213> ORGANISM: Artificial Sequence
<220> FEATURE:
<223> OTHER INFORMATION: forward primer

<400> SEQUENCE: 6
atgagacagg agcatcgggt ggacataccc gagaacttgt ggttcatgtg cagctccatc    60

<210> SEQ ID NO 7
<211> LENGTH: 59
<212> TYPE: DNA
<213> ORGANISM: Artificial Sequence
<220> FEATURE:
<223> OTHER INFORMATION: reverse primer

<400> SEQUENCE: 7
tcacgttcga ggcgcattcg acgccggata gtgacgatgt gagctcagcc aatcgactg     59

<210> SEQ ID NO 8
<211> LENGTH: 60
<212> TYPE: DNA
<213> ORGANISM: Artificial Sequence
<220> FEATURE:
<223> OTHER INFORMATION: forward primer

<400> SEQUENCE: 8
gtgatcgata tttccgctca accctcgcag cagagcacgt ggttcatgtg cagctccatc    60

<210> SEQ ID NO 9
<211> LENGTH: 59
<212> TYPE: DNA
<213> ORGANISM: Artificial Sequence
<220> FEATURE:
<223> OTHER INFORMATION: reverse primer

<400> SEQUENCE: 9
tcaaaagact ctccccgcaa cgatggcgac gagcacgagt gagctcagcc aatcgactg    59

<210> SEQ ID NO 10
<211> LENGTH: 60
<212> TYPE: DNA
<213> ORGANISM: Artificial Sequence
<220> FEATURE:
<223> OTHER INFORMATION: forward primer

<400> SEQUENCE: 10
gtgcgcacgg agtcgcgcag cctggcccag ttcgtggcgt ggttcatgtg cagctccatc    60

<210> SEQ ID NO 11
<211> LENGTH: 59
<212> TYPE: DNA
<213> ORGANISM: Artificial Sequence
<220> FEATURE:
<223> OTHER INFORMATION: reverse primer

<400> SEQUENCE: 11
tcatgcgtcg tggacggcgt ctcgatcgag gagacacggt gagctcagcc aatcgactg    59

<210> SEQ ID NO 12
<211> LENGTH: 60
<212> TYPE: DNA
<213> ORGANISM: Artificial Sequence
<220> FEATURE:
<223> OTHER INFORMATION: forward primer

<400> SEQUENCE: 12
atgccgaact ctcccgccgc ggtcttcgag cggctcacct ggttcatgtg cagctccatc    60

<210> SEQ ID NO 13
<211> LENGTH: 59
<212> TYPE: DNA
<213> ORGANISM: Artificial Sequence
<220> FEATURE:
<223> OTHER INFORMATION: reverse primer

<400> SEQUENCE: 13
tcacgtcgtc tccatcatcg tgtactcctg ccggatccgt gagctcagcc aatcgactg    59

<210> SEQ ID NO 14
<211> LENGTH: 60
<212> TYPE: DNA
<213> ORGANISM: Artificial Sequence
<220> FEATURE:
<223> OTHER INFORMATION: forward primer

<400> SEQUENCE: 14
atgggccaga cgacgcacac agcactcgac cgctacatgt ggttcatgtg cagctccatc    60

<210> SEQ ID NO 15
<211> LENGTH: 59
<212> TYPE: DNA
<213> ORGANISM: Artificial Sequence
<220> FEATURE:
<223> OTHER INFORMATION: reverse primer

<400> SEQUENCE: 15
tcagcccggc gtacgggtgt accggttgcg caggttcgtt gagctcagcc aatcgactg    59

<210> SEQ ID NO 16
<211> LENGTH: 35
<212> TYPE: DNA
<213> ORGANISM: Artificial Sequence

```
<220> FEATURE:
<223> OTHER INFORMATION: forward primer

<400> SEQUENCE: 16
gctctagacg gctggagtgt agcgagtctg gaatg                              35

<210> SEQ ID NO 17
<211> LENGTH: 29
<212> TYPE: DNA
<213> ORGANISM: Artificial Sequence
<220> FEATURE:
<223> OTHER INFORMATION: reverse primer

<400> SEQUENCE: 17
ggaattcccc ggacgtggga gcgataggg                                     29

<210> SEQ ID NO 18
<211> LENGTH: 24
<212> TYPE: DNA
<213> ORGANISM: Artificial Sequence
<220> FEATURE:
<223> OTHER INFORMATION: K43R-F

<400> SEQUENCE: 18
caccaccccg aggaagccga actc                                          24

<210> SEQ ID NO 19
<211> LENGTH: 24
<212> TYPE: DNA
<213> ORGANISM: Artificial Sequence
<220> FEATURE:
<223> OTHER INFORMATION: K43R-R

<400> SEQUENCE: 19
gagttcggct cctcggggt ggtg                                           24

<210> SEQ ID NO 20
<211> LENGTH: 25
<212> TYPE: DNA
<213> ORGANISM: Artificial Sequence
<220> FEATURE:
<223> OTHER INFORMATION: K88E-F

<400> SEQUENCE: 20
ggccgtgtgg aggacctgcc gggtg                                         25

<210> SEQ ID NO 21
<211> LENGTH: 25
<212> TYPE: DNA
<213> ORGANISM: Artificial Sequence
<220> FEATURE:
<223> OTHER INFORMATION: K88E-R

<400> SEQUENCE: 21
cacccggcag gtcctccaca cggcc                                         25

<210> SEQ ID NO 22
<211> LENGTH: 25
<212> TYPE: DNA
<213> ORGANISM: Artificial Sequence
<220> FEATURE:
<223> OTHER INFORMATION: L90K-F

<400> SEQUENCE: 22
gtgtgaagga caagccgggt gtccg                                         25
```

<210> SEQ ID NO 23
<211> LENGTH: 25
<212> TYPE: DNA
<213> ORGANISM: Artificial Sequence
<220> FEATURE:
<223> OTHER INFORMATION: L90K-R

<400> SEQUENCE: 23
cggacacccg gcttgtcctt cacac                                          25

<210> SEQ ID NO 24
<211> LENGTH: 520
<212> TYPE: PRT
<213> ORGANISM: Streptomyces xiamenensis

<400> SEQUENCE: 24

```
Met Arg Gln Glu His Arg Val Asp Ile Pro Glu Asn Leu Thr Arg Arg
1               5                   10                  15

Trp Ala Glu His Ala Arg Glu Lys Gly Trp Ser Glu Arg Thr Ala Phe
            20                  25                  30

His Ala Asp Gly Arg Ala Trp Thr Phe Ala Glu Val Phe Asp Gly Ala
        35                  40                  45

Ala Arg Val Ala Ala Gly Tyr Arg Ser His Gly Leu Arg Thr Gly Asp
    50                  55                  60

Arg Val Leu Leu Ala Leu Pro Asp Ser Val Glu Met Val Trp Cys Leu
65                  70                  75                  80

Leu Gly Ala Trp Gln Ala Gly Leu Val Ala Val Pro Val Asn Val Gln
                85                  90                  95

Met Ser Arg Met Asp Leu Thr Arg Asp Val Val Thr Ala Glu Pro Ala
            100                 105                 110

Leu Val Val Val Asp Pro Glu Thr Ala Gly Trp Leu Gly Asp Ser Gly
        115                 120                 125

Pro Ala Pro Thr Thr Glu Val Val Pro Leu Val Ala Ala Glu Pro Glu
    130                 135                 140

Glu Ala Phe Ala Thr Gly Gly Asn Ala Ala Ala Leu Ala Val Phe Thr
145                 150                 155                 160

Ser Gly Thr Thr Gly Ala Pro Lys Leu Cys Phe Phe Arg His Arg Asp
                165                 170                 175

Leu Gly Ala Pro Arg Ala Pro Gly Leu Val Ser Gly Pro Asp Thr Val
            180                 185                 190

Gly Leu Ser Val Ser Arg Met Tyr Phe Val Gly Gly Leu Ser Ala Ser
        195                 200                 205

Val Phe Thr Thr Leu Glu Thr Gly Gln Val Ala Val Leu Ser Arg Pro
    210                 215                 220

Arg Ala Thr Pro Ala Ala Val Glu Leu Met Arg Arg His Asn Val
225                 230                 235                 240

Thr Val Leu Phe Ala Gln Pro Ser Phe Leu Ala Arg Leu Leu Leu Glu
                245                 250                 255

Pro Gly His Ala Glu Val Leu Gly Asn Val Arg Gln Ala Phe Cys Ala
            260                 265                 270

Gly Glu Val Phe Thr Ala Arg Leu Arg Glu Gln Leu Val Pro Ile Met
        275                 280                 285

Gly Pro Arg Leu Leu Asn Thr Tyr Gly Thr Thr Glu Ala Gly Ala Val
    290                 295                 300

Ala Val Gly Pro Pro Ala Val Tyr Asp Val Pro Ser Ala Val Gly Pro
305                 310                 315                 320
```

```
Pro Leu Pro Gly Arg Pro Val Arg Val Val Asp Ala Asp Gly His Glu
            325                 330                 335

Leu Pro Thr Gly Ser Met Gly Glu Leu His Ile Arg Val Pro Ile Ala
            340                 345                 350

Thr Arg Gly Val Ala His Gly Ser Leu Gly Pro Asp Ile Leu Thr Asp
            355                 360                 365

Val Trp Trp Pro Thr Gly Asp Leu Ala Ser Ile Asp Glu Asn Gly Val
        370                 375                 380

Val His Ala His Gly Arg Leu Asp Asp Ile Glu Val Ile Gly Gly Gln
385                 390                 395                 400

Asn Leu Val Pro Ser Glu Val Glu Arg Leu Leu Glu Ser His Pro Arg
            405                 410                 415

Val Leu Glu Ala Ala Val Ser Ser Val Trp Arg Pro Ala Gly Asp Thr
            420                 425                 430

Ser Leu Arg Ala Tyr Val Val Ala Ala Ala Pro Gly Ser Ser Asp
            435                 440                 445

Glu Gly Pro Val Arg Gly Asp Asp Ala Leu Ala Ala Glu Leu Val Glu
            450                 455                 460

Leu Ala Arg Ser Thr Leu Ser Trp Tyr Lys Val Pro Gln Asp Val Val
465                 470                 475                 480

Trp Leu Asp Thr Leu Pro Arg Asn Gly Asn Gly Lys Leu Leu Arg Arg
            485                 490                 495

Val Leu Arg Ala Gln Gly Asp Glu Phe Ile Gln Pro His Arg His Tyr
            500                 505                 510

Pro Ala Ser Asn Ala Pro Arg Thr
            515                 520

<210> SEQ ID NO 25
<211> LENGTH: 313
<212> TYPE: PRT
<213> ORGANISM: Streptomyces xiamenesis

<400> SEQUENCE: 25

Val Ile Asp Ile Ser Ala Gln Pro Ser Gln Gln Ser Thr Arg Tyr Arg
1               5                   10                  15

Phe Val Val Pro Ser Ile Ala Ala Ser Val Val Pro Ser Ala Pro Lys
            20                  25                  30

Ala Val Leu Pro Tyr Leu Gln Leu Ala Arg Met His Ala Pro Ile Gly
            35                  40                  45

Ser Trp Leu Tyr Leu Leu Pro Gly Leu Trp Ile Ala Leu Ala Ser
    50                  55                  60

Ala Gly Leu Pro Asp Trp Arg Gln Val Leu Leu Phe Thr Val Gly Gly
65                  70                  75                  80

Val Leu Val Arg Gly Phe Gly Cys Val Val Asn Asp Leu Ala Asp Arg
            85                  90                  95

Lys Phe Asp Ala Arg Val Ala Arg Thr Val Gly Arg Pro Leu Val Ala
            100                 105                 110

Gly Thr Val Thr Val Thr Gly Ala Leu Val Phe Ala Val Gln Ala
            115                 120                 125

Val Ala Gly Leu Leu Val Leu Ala Ala Ser Val Pro Ala Ala Val
            130                 135                 140

Phe Val Ala Ala Ser Tyr Pro Leu Val Val Ala Tyr Pro Phe Met Lys
145                 150                 155                 160

Arg Ile Thr Tyr Trp Pro Gln Ala Trp Leu Gly Met Val Phe Gly Cys
```

```
                165                 170                 175
Tyr Ile Leu Ala Gly Trp Leu Ala Val Ala Gly Arg Ile Glu Thr Pro
            180                 185                 190
Ala Leu Leu Phe Val Ala Gly Val Phe Trp Thr Leu Gly Tyr Asp
        195                 200                 205
Thr Ile Tyr Ala His Gln Asp Lys Ala Asp Val Gln Val Gly Val
    210                 215                 220
Lys Ser Leu Ala Leu Arg Leu Gly Arg Ala Thr Arg Pro Trp Val Ala
225                 230                 235                 240
Gly Phe Tyr Gly Ala Thr Val Val Gly Ile Val Ala Ala Gly Ala Val
                245                 250                 255
Ala Asp Leu His Trp Thr Phe Tyr Ala Leu Phe Leu Pro Gly Val Ala
            260                 265                 270
His Leu Leu Trp Gln Val Val Thr Val Asp Ile Asp Ser Pro Ala Asp
        275                 280                 285
Cys Arg Glu Lys Phe Met Ala Asn Arg Phe Gly Trp Leu Val Leu
    290                 295                 300
Val Ala Ile Val Ala Gly Arg Val Phe
305                 310
```

<210> SEQ ID NO 26
<211> LENGTH: 196
<212> TYPE: PRT
<213> ORGANISM: Streptomyces xiamenesis

<400> SEQUENCE: 26

```
Val Arg Thr Glu Ser Arg Ser Leu Ala Gln Phe Val Ala Leu Leu Arg
1               5                   10                  15
Glu Pro Ala Ser Leu Ala Thr Glu Val Leu Glu Glu Trp Cys Gly Ala
            20                  25                  30
Pro Val Thr Ala Glu Ile Arg His Arg Ala Asp Gly Gln Leu Leu Val
        35                  40                  45
Pro Pro Ala Glu Arg Thr Phe Gly Gly Gly Ser Ala Gln Ala Glu Arg
    50                  55                  60
Ala Pro Phe Leu Pro Pro Glu Arg Val Ala Glu Leu Met Arg Leu Ser
65                  70                  75                  80
Thr Gly Ala Arg Val Gln Phe Arg Thr Val Tyr Leu Arg Ala Gly Thr
                85                  90                  95
Glu Lys Val Val Thr Ala Gly Ala Val Val Ala Leu Glu Arg Ile Ser
            100                 105                 110
Pro Glu Glu His Ala Val Leu Ser Thr Thr Asn Ala Pro Leu Gly Pro
        115                 120                 125
Val Leu Ala Ala Gly Gly Val Arg Arg Val Met Val Thr Ser Glu
    130                 135                 140
Pro Thr Arg Leu Asp Pro Ala Val Arg Pro Pro Cys Asp Ala Asp Ala
145                 150                 155                 160
Pro Val Leu Thr Val Thr Ala Leu Leu Cys Arg Gly Thr Met Pro Val
                165                 170                 175
Gly Leu Val Arg Glu Ala Phe Leu Pro Cys Leu Leu Asp Arg Asp Ala
            180                 185                 190
Val His Asp Ala
        195
```

<210> SEQ ID NO 27
<211> LENGTH: 473

```
<212> TYPE: PRT
<213> ORGANISM: Streptomyces xiamenesis

<400> SEQUENCE: 27

Met Pro Asn Ser Pro Ala Ala Val Phe Glu Arg Leu Thr Thr Thr Val
1               5                   10                  15

Pro Pro Val Arg Ile Glu Val Arg Leu Gly Thr Ala Cys Val Leu Gly
            20                  25                  30

Gly Gly Val Ala Gly Leu Val Ala Ala Arg Val Leu Ala Asp His Ala
        35                  40                  45

Asn Arg Val Val Ile Ile Glu Pro Asp Leu Pro Glu Ala Ala Leu Ser
    50                  55                  60

Gly Ala Ala Arg Pro Gly Val Pro Gln Gly Ser Gln Val His Leu Leu
65                  70                  75                  80

Leu Pro Gly Gly Arg Ala Gln Leu Glu Arg Phe Phe Pro Gly Val Val
                85                  90                  95

Ala Glu Ala Leu Ala Gly Gly Ala Val Ser Cys Gly Pro Glu Arg Thr
            100                 105                 110

Ala Thr Tyr Leu Asp Asp Ile Glu Gln Ile Ala Thr Pro Asn Ala Arg
        115                 120                 125

Phe Leu Gly Ser Ser Arg Pro Phe Leu Glu Thr Leu Ile Arg Arg Arg
130                 135                 140

Ala Leu Ala Leu Pro Asn Val Glu Leu Val Ser Gly Arg Val Ile Gly
145                 150                 155                 160

Leu Arg Tyr Ala Arg Gly Ala Val Glu Ser Val Arg Tyr Ala Val Gly
                165                 170                 175

Gly Asp His Val Val Ala Pro Ala Asp Phe Val Val Asp Ala Ser Gly
            180                 185                 190

Arg Gly Ser Arg Leu Ser Asp Trp Leu Glu Gln Gly Gly Trp Pro Arg
        195                 200                 205

Pro Glu Thr Gln Arg Leu Gln Thr Asp Ile Arg Tyr Leu Ser Ala Arg
    210                 215                 220

Phe Thr Arg Ser Ala Asp Trp Asp Gly Pro Leu Ser Gly Ile Ser Arg
225                 230                 235                 240

Tyr Ser Pro His Phe Pro Lys Asp Ile Ala Gly Ala Val Asn Pro
                245                 250                 255

Ile Glu Asn Gln Gln Trp Val Val Met Leu Ala His Phe Gly Asn Gly
            260                 265                 270

Ala Glu Gly Arg Thr Ala Asp Glu Phe Val Ala Arg Cys Arg Glu Leu
        275                 280                 285

Pro Pro Ile Phe Gln Glu Ala Val Lys Gly Glu Ile Val Gly Glu Val
    290                 295                 300

Val Pro Tyr Arg His Pro Asp Ser Arg Trp Arg His Phe Glu Ala Leu
305                 310                 315                 320

Asp Arg Phe Pro Ala Arg Leu Ala Val Leu Gly Asp Ala Val Ala Ser
                325                 330                 335

Phe Asn Pro Leu Tyr Gly Gln Gly Met Ser Ser Ala Ala Leu His Ala
            340                 345                 350

Ser Cys Leu Ser Glu Phe Leu Arg Ser Gly Pro Asp Leu Asp Ala Pro
        355                 360                 365

Ala Arg His Phe Leu Glu Leu Glu Lys Val Val Val Glu Ala Ala Trp
    370                 375                 380

Gln Thr Ser Thr Ala Gly Asp Ala Ile Arg Leu Gly Leu Ala Thr Pro
385                 390                 395                 400
```

```
Pro Ala Thr Asp Gln Gly Arg Arg Gln Ala Trp Ala Leu Arg Gln Val
            405                 410                 415

Arg Glu Ala Ala Gly Arg Asp Glu Gln Val Gly Thr Ala Leu Arg Ala
            420                 425                 430

Val Gly Phe Met Thr Ala His Pro Ala Ser Leu Met Ala Pro Asp Leu
            435                 440                 445

Val Leu Arg Ala Ala Arg Val Asn Gly Val Pro Glu Glu Arg Ile Arg
    450                 455                 460

Gln Glu Tyr Thr Met Met Glu Thr Thr
465                 470

<210> SEQ ID NO 28
<211> LENGTH: 124
<212> TYPE: PRT
<213> ORGANISM: Streptomyces xiamenesis

<400> SEQUENCE: 28

Met Gly Gln Thr Thr His Thr Ala Leu Asp Arg Tyr Met Glu Leu Ala
1               5                   10                  15

Asp Arg Ala Val Arg Asp Pro Ser Ala Leu Ala Glu Leu Pro Thr Ile
            20                  25                  30

Phe Ala Pro Asp Ala Thr Val Thr Leu Arg Asp Glu Pro Val Thr Gly
            35                  40                  45

Met Pro Ala Ile Met Glu Phe Tyr Arg Val Phe Val Ala Ala Val Ala
    50                  55                  60

Glu Ser Lys His Tyr Trp Thr Thr Thr Ile Leu Glu Asp Gly Thr Ile
65                  70                  75                  80

Glu Ser His Trp Val Val Ala Ala Arg Arg Ala Asp Gly Ser Leu Met
            85                  90                  95

Thr Ala Ala Gly Val Glu His Ala Thr Val Asp Thr Asp Gly Leu Ile
            100                 105                 110

Thr Asn Leu Arg Asn Arg Tyr Thr Arg Thr Pro Gly
            115                 120
```

CLONE OF XIAMENMYCIN BIOSYNTHESIS GENE CLUSTER AND HETEROLOGOUS EXPRESSION THEREOF

CROSS REFERENCE OF RELATED APPLICATION

This is a U.S. National Stage under 35 U.S.C 371 of the International Application PCT/CN2014/075784, filed Apr. 21, 2014, which claims priority under 35 U.S.C. 119(a-d) to CN 201310273055.5, filed Jul. 1, 2013.

BACKGROUND OF THE PRESENT INVENTION

Field of Invention

The present invention belongs to biotechnology, involves a Xiamenmycin biosynthesis gene cluster, its application and the bacterial strains harboring the hereinbefore mentioned Xiamenmycin biosynthesis gene cluster for producing Xiamenmycin.

Description of Related Arts

The model strain of *Streptomyces xiamenensis* was isoloated from mangrove sediments in Xiamen, Fujian Province, China, in whose fermentation broth a kind of benzopyran compound was found:

N-[[3,4-dihydro-3S-hydroxy-2S-methyl-2-(4'R-methyl-3'S-pentenyl)-2H-1-benzopyran-6-yl]carbonyl]-threonine, constitutional formula is as below:

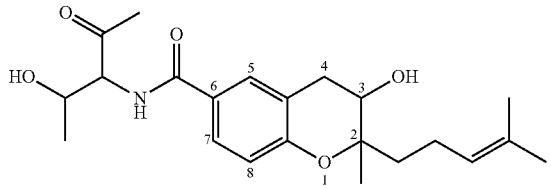 [SMILES: CC(=O)C(NC(=O)c1ccc2c(c1)CC(O)C(C)(CCC=C(C)C)O2)C(C)O]

The chemical structure of this compound can be divided into three parts: L-threonine, 4-hydroxybenzoic acid and Geranyl group. This kind of compound has low cellular toxicity, and high membrane penetrability. It is reported that this compound can restrain the cell adhesion of ICAM-1 (intercellular adhesion molecule-1)/LFA-1 (lymphocyte functional related antigen) mediation, and has the potential to be developed into anti-inflammatory and anti-fibrosis drug. The main sources of the benzopyran compound which is replaced by isopentene group: phytoextraction, chemical synthesis, and chemoenzymatic synthesis. The present invention involves microbial cultivation to produce this kind of compound.

SUMMARY OF THE PRESENT INVENTION

The purpose of the present invention is to provide a kind of Xiamenmycin biosynthesis gene cluster, its application and related bacterial strain, specifically by the method of cloning and obtaining benzopyran compound (xiamenmycin) from *Streptomyces xiamenensis*, by heterologous expression to produce xiamenmycin compound in other *streptomyces*, and to improve the titre of the compound by introducing the antibiotics resistance.

The purpose of invention is realized by the following technical proposal:

Firstly, the present invention involves a Xiamenmycin biosynthesis gene cluster with a nucleotide sequence showed as SEQ ID NO.1, with a whole length of 5189 bp.

Preferably, the Xiamenmycin biosynthesis gene cluster as hereinbefore defined includes genes ximA, ximB, ximC, ximD and ximE as below:

ximA: situated at No. 1-1563 base pairs of the SEQ ID NO.1, encoding 520 amino acids;

ximB: situated at No. 1788-2729 base pairs of the SEQ ID NO.1, encoding 313 amino acids;

ximC: situated at No. 2795-3385 base pairs, encoding 196 amino acids;

ximD: situated at No. 3394-4815 base pairs, encoding 473 amino acids;

ximE: situated at No. 4815-5189 base pairs, encoding 124 amino acids;

Secondly, the present invention involves a new application of the Xiamenmycin biosynthesis gene cluster as hereinbefore defined in the production of Xiamenmycin.

Thirdly, the present invention involves a *Streptomyces xiamenensis* strain CGMCC No. 5670.

Fourthly, the present invention involves a mutant strain of the *Streptomyces xiamenensis* CGMCC No. 5670 as hereinbefore defined produced by introducing a mutant rpsL gene into the *Streptomyces xiamenensis* as hereinbefore defined.

Preferably, the mutant strain as hereinbefore defined includes *Streptomyces xiamenensis* strain CGMCC No. 5674, *Streptomyces xiamenensis* strain CGMCC No. 5675 and *Streptomyces xiamenensis* strain CGMCC No. 5676.

Fifthly, the invention involves a method to produce the Xiamenmycin, comprising steps of: selecting a strain or with a genetic engineering micribial strain carring the Xiamenmycin biosynthesis gene cluster, then fermenting to produce the Xiamenmycin.

The clone of Xiamenmycin biosynthesis gene cluster and its heterologous expression in the invention are described as follows:

Firstly, extract a chromosomal DNA of Streptomycete, then construct a fosmid library;

Secondly, one fosmid (p9A11), which has been shown to cover a complete biosynthetic gene cluster, was obtained by PCR amplification with a primer targeted specially for prenyltransferase;

Thirdly, a 7.5 kb HindIII-XbaI fragment is amplified from the fosmid p9A11 and cloned into pJTU1278 to generate plasmid pLMO09403 harboring the complete xiamenmycin gene cluster;

Fourthly, knock out ximA, ximB, ximC, ximD and ximE in the gene cluster using a PCR targeting technology; then introduce the mutated plasmid into the original strain and knockout a corresponding gene;

Fifthly, disappearance of benzopyran compounds in a supernatant after culturing the ximB, ximC, ximD and ximE mutant strains was confirmed by HPLC, while culturing ximA mutant strain generates a metabolic intermediate Xiamenmycin B; therefore, it proves that the gene cluster is the biosynthetic gene cluster of Benzopyran compounds Xiamenmycin;

Sixthly, isolate and purify the Xiamenmycin B from the fermented supernatant of the ximA by HPLC; then identify a compound, wherein a chemical structure is as show in FIG. 1 (G);

Seventhly, the entire Xiamenmycin biosynthetic gene cluster is inserted into pSET152 to yield pLMO09404. The plasmid is introduced into *Streptomyces lividans* strain 1326, and then Xiamenmycin was detected in a ferment broth;

Eighthly, clone the gene encoding a ribosomal protein S12 from *Streptomyces xiamenensis*, and the gene is subjected to site-directed mutagenesis using PCR to generate point mutations: rpsL-K43R, K88E and L90K respectively;

Ninthly, the mutated rpsL genes are inserted into pIB139, an integrative expression vector in *Streptomyces*; these plasmids are transformed into *E. coli* ET12567: pUZ8002 separately and used as donor strains for two parental *E. coli-Streptomyces* conjugations; and then obtain the mutant strains with an increased production of benzopyran compound Xiamenmycin.

The mutant strains in the present invention belong to the *Streptomyces xiamenensis* as mentioned above. A feature of mutant strains is a plasmid which carries a mutant rpsL gene and its amino acid with three mutant types, namely, K43R, K88E, and L90K individually.

A nucleotide sequence or partial nucleotide sequence provided in the present invention is able to be obtained by a method of polymerase chain reaction (PCR) or microbial genomic library by southern hybridization with the DNA sequence in the present invention as a probe to obtain benzopyran compound antibiotic biosynthesis gene cluster.

The present invention also provides a method that isolates the benzopyran compound biosynthetic gene from the microbial genomic library.

The nucleotide sequence or many other sequences provided here are able to be cloned into vectors so as to produce other recombinant sequences and DNAs.

The cloned genes of the sequences and at least partial sequences in the present invention are able to be expressed in foreign hosts through proper expression systems to obtain corresponding products. These foreign hosts include *streptomyces, Escherichia coli, Bacillus*, yeast, plant and animal cell, etc.

The *Streptomyces xiamenensis* in the present invention has been deposited to the China General Microbiological Culture Collection Center (CGMCC), and preserved within in 29 Dec. 2011. Address: No. 3, No. 1 Yard, West Beicheng Road, Chaoyang District, Peking, Institute of Microbiology of Chinese academy of Sciences, Culture Preservation No.: CGMCC No. 5670.

The mutant strains, 3 types of antibiotic-resistant mutant strains of the *Streptomyces Xiamenensis*, have also been deposited in the China General Microbiological Culture Collection Center (CGMCC), and preserved within in 29 Dec. 2011. Address: No. 3, No. 1 Yard, West Beicheng Road, Chaoyang District, Peking, Institute of Microbiology of Chinese Academy of Sciences, culture preservation numbers: CGMCC No. 5674, CGMCC No. 5675 and CGMCC No. 5676.

The profit of the present invention: The present invention provides the strain sources by using the *Streptomyces xiamenensis*, its mutant strain and genetically engineered microbial strains carring the gene cluster of Xiamenmycin biosynthesis to produce the benzopyran compound through biosynthesis; the mutant strain is able to be used in industrial production.

BRIEF DESCRIPTION OF THE DRAWINGS

Features, purposes and advantages of the present invention would be more distinctive through reading and referring to the below attached figures that explain the non-restrictive examples.

in which: A is HPLC profile of fermentation products of wild-type *Streptomyces lividans* after introducing pLMO09404; B is HPLC profile of fermentation products of wild-type *Streptomyces lividans*.

Figure 3:
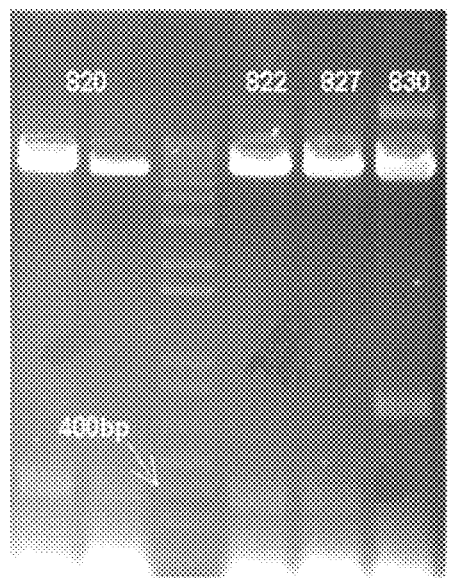

FIG. 3: insertion of 3 mutant rpsL genes into the expression vector pIB139 was confirmed by restriction enzyme digestion analysis.

Figure 4:
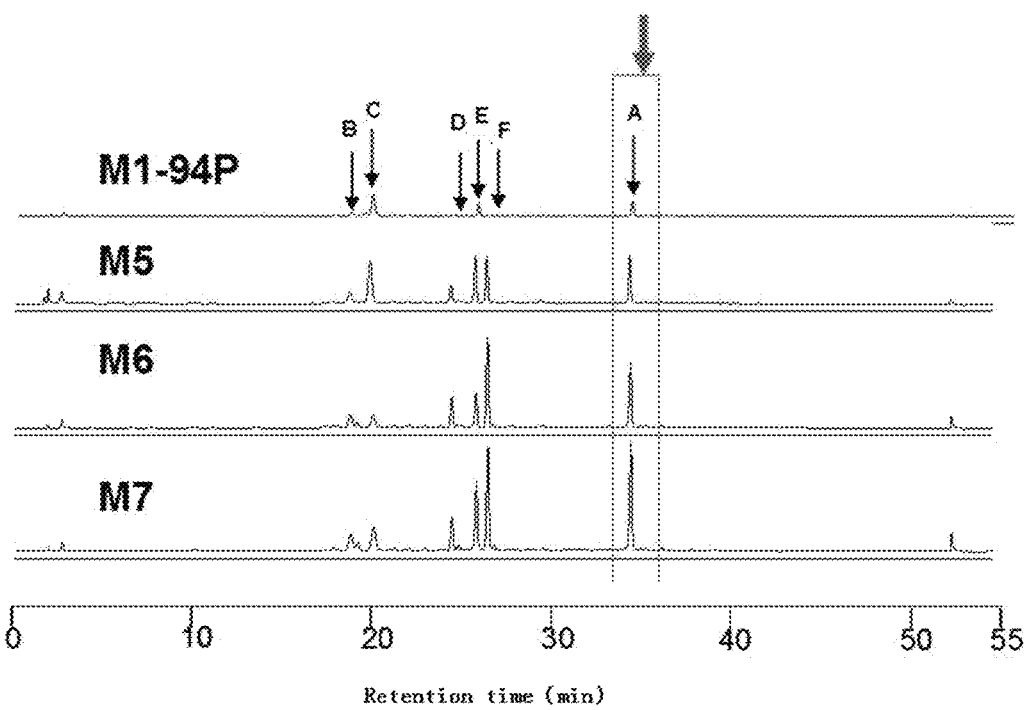

FIG. 4: HPLC profiles of the mutants generated by PCR site-directed mutagenesis shows increased Xiamenmycin production.

DETAILED DESCRIPTION OF THE PREFERRED EMBODIMENT

Detailed explanation would be conducted with attached figures and preferred embodiments. The following preferred embodiments could help the technicians to further understand the present invention, but would not confine the present invention in any form. Indicated here that in the precondition that not breaking away from concept of the present invention, the technicians could do some adjustments and improvement. These all belong to the protection domain of the present invention. In the following examples, those with no indication of actual experiment conditions, shall be conducted with normal conditions and the suggestions by the manufacturer.

The present invention relates to a method of cloning and obtaining benzopyran compound (Xiamenmycin) from *Streptomyces xiamenensis*, and through heterologous expression of xiamenmycin biosynthesis gene cluster to produce compound in other *Streptomyces*, and a method to improve a yield of the compound by introducing antibiotics-resistance to a producing strain.

Specific explanation: according to a structure feature of a target compound and feeding of a hydroxybenzoic acid (4-HBA) indicated by $C^{13}$, it is proved that 4-HBA is one of precursors of benzopyran compound's biosynthesis. According to existing of isopentenyl transferase in the biosynthesis of benzopyran compound, its candidate biosynthesis gene cluster is confirmed to exist in *Streptomyces xiamenensis* strain 318 by bioinformatic analysis. Design primers based on isopentenyl transferase gene cluster, amplify using PCR and screen from *Streptomyces xiamenensis* 318 genomic library, then obtain positive fosmid clone p9A11. Carry out gene disruption experiment base on a 5188 by DNA fragment on p9A11, and it is proved that deleting an isopentenyl transferase on the *Streptomyces xiamenensis* is able to block biosynthesis of the target benzopyran compound. The gene cluster was cloned into vector pSET152, then transformed into *Streptomyces lividans* for heterologous expression, then the Xiamenmycin is able to be detected in a host's fermentation supernate. Clone the gene rpsL of ribosomal S12 in *Streptomyces xiamenensis* to carry out external PCR site-directed mutagenesis and clone the mutant rpsL gene into Streptomycete integratative vector and transformed it into *Streptomyces xiamenensis* by *E. coli*-streptomycete conjugation and obtain increased yield of xiamenmycin in the mutant strain. The specific process, see as below.

Example 1, Cloning and Heterologous Expression of the Xiamenmycin Biosynthesis Gene Cluster Firstly, extract DNA of *Streptomyces xiamenensis* (CG-MCC No. 5670), and construct a fosmid library.

Add 500 μL lysozyme solution to suspend 5 mg mycelium and incubate in 37° C. till it turns to translucent;

Add 20% SDS with 50% volume, mix until a viscosity of the solution decreases significantly, then add in neutral phenol/chloroform with a same volume, mix it well. And then centrifuged at 12000 rpm for 5 min, a supernatant is collected and a white interlayer is discarded;

Repeat the procedure as mentioned above till the interlayer is hard to be seen. Finally, add 3 M acetate (natural pH, 0.1:1, v:v,) and isopropanol (1:1, v:v) respectively. Mix them upside-down till a white flocculent DNA appears. Use glass rod to pick out the DNA and use 70% ethyl alcohol to wash the DNA for 2 times. Discard all the supernate and add a TE buffer solution to dissolve the DNA after ethyl alcohol has been volatilized.

Construct the fosmid library using a CopyControl™ Fosmid Library Production Kit (EPICENTRE Biotechnologie).

Secondly, according to a genome mining result, design PCR primers that targeting prenyltransferase, use PCR amplification to screen a positive cloned p9A11.

Use fosmid plasmid as a PCR template and use primer YY-318-5313 to select a positive clone that carring prenyltransferase:

```
Forward:  5'-TGGCTGGGGATGGTCTTCG-3';  (SEQ ID NO. 2)

Reverse:  5'-CCTTGTCCTGGTGGGCGTA-3'.  (SEQ ID NO. 3)
```

20 μL amplified reaction includes 9 μL ddH2O, 2 μL 10×PCR Buffer, 1 μL DMSO, each primer (20 μM) 1 μL, 4 μL dNTP (each 2.5 mM), 1 μL Taq enzyme (1 unit/μL), 1 μL DNA in total. PCR amplification conditions: initial 3 min denaturation at 95° C., then 1 min denaturation at 94° C., 1 min annealing at 55° C., 1 min extension at 72° C., 30 cycles in total, final 10 min extension at 72° C.

After AGE (agarose gel electrophoresis) separation, a size of the PCR products was about 200 bp.

Thirdly, a 7.5 kb fragment was amplified from fosmid p9A11 and cloned into pJTU1278 to generate plasmid pLMO09403 harboring a complete xiamenmycin gene cluster;

Using p9A11 as a template for primer design:

```
Forward primer:
                                          (SEQ ID NO. 4)
5'-GCTCTAGACGGCTGGAGTGTAGCGAGTCTGGAATG-3', Reverse primer:
                                          (SEQ ID NO. 5)
5'-GGAATTCCCCGGACGTGGGAGCGATAGGG-3'.
```

A PCR product is about 7.5 kb, covering the whole gene cluster. Use high success ratio PCR enzyme KOD FX.

PCR system: 2×PCR Buffer 25 μL; 2 mM dNTP 10 μL; primer 10 pmol/μL, each for 1.5 μL; template 150 ng/μL 1 μL; KOD FX 1 μL; water 10 μL.

The circulation condition of PCR: Initial 2 min denaturation at 94° C., then 10 sec denaturation at 98° C., 8 min extension at 68° C., 40 circulations in total; final heat preservation at 4° C.

7.5-kb DNA fragment was recovered after 1% Agarose Gel Electrophoresis of PCR products and this fragment was ligated to a vector pMD18-T. Ligation conditions: insert fragment 2 μL (158 ng/μL), vector 3 μL (50 ng/μL), solution-I 5 μL, 16° C., 15 h.

The positive clone that harbored prenyltransferase was found in the transformed *E. coli* DH5α using colony PCR and restriction enzyme digestion. The plasmid was digested by XbaI and HindIII and was further purified and separated using 1% AGE. The 7.5 kb XbaI-HindIII DNA fragment was recovered and ligated with a vector pJTU1278, which also digested by corresponding restriction enzyme digestion. Ligation conditions: insert fragment 3 μL (134 ng/μL), vector 2 (114 ng/μL), solution-I 5 μL, 16° C., 15 h.

After the positive clone that carried prenyltransferase was found in the transformants of *E. coli* DH5α, colony PCR colony and the restriction enzyme digestion were used in further verification. In XbaI and HindIII double digestion, the vector and insert fragments shall also conform to a theoretical size.

Fourthly, use a PCR-Targeting technology to knock out ximA, ximB, ximC, ximD, ximE of the gene cluster and introduce a mutant plasmid into the *Streptomyces* strains, knockout corresponding genes.

Transformed pLMO09403 plasmid into the *E. coli* BW25113 with a chemical transformation method;

Design primer to replace a corresponding open-reading-frame.

Gene replacement of the ximA,

```
Forward primer (SEQ ID NO. 6):
5'-
ATGAGACAGGAGCATCGGGTGGACATACCCGAGAACTTGTGGTTCATGTG

CAGCTCCATC-3',

Reverse primer (SEQ ID NO. 7)
5'-

TCACGTTCGAGGCGCATTCGACGCCGGATAGTGACGATGTGAGCTCAGCC

AATCGACTG-3',
```

Gene replacement of the ximB,

```
Forward primer (SEQ ID NO. 8):
5'-

GTGATCGATATTTCCGCTCAACCCTCGCAGCAGAGCACGTGGTTCATGTG

CAGCTCCATC-3',

Reverse primer (SEQ ID NO. 9):
5'-

TCAAAAGACTCTCCCCGCAACGATGGCGACGAGCACGAGTGAGCTCAGCC

AATCGACTG-3',
```

Gene replacement of the ximC,

Forward primer (SEQ ID NO. 10):
5'-GTGCGCACGGAGTCGCGCAGCCTGGCCCAGTTCGTGGCGTGGTTCATGTGCAGCTCCATC-3', Reverse primer (SEQ ID NO. 11):
5'-TCATGCGTCGTGGACGGCGTCTCGATCGAGGAGACACGGTGAGCTCAGCCAATCGACTG-3', Gene replacement of the ximD, Forward primer (SEQ ID NO. 12):
5'-TCATGCGTCGTGGACGGCGTCTCGATCGAGGAGACACGGTGAGCTCAGCCAATCGACTG-3', Reverse primer (SEQ ID NO. 13):
5'-TCACGTCGTCTCCATCATCGTGTACTCCTGCCGGATCCGTGAGCTCAGCCAATCGACTG-3', Gene replacement of the ximE, Forward primer (SEQ ID NO. 14):
5'-ATGGGCCAGACGACGCACACAGCACTCGACCGCTACATGTGGTTCATGTGCAGCTCCATC-3', Reverse primer (SEQ ID NO. 15):
5'-TCAGCCCGGCGTACGGGTGTACCGGTTGCGCAGGTTCGTTGAGCTCAGCCAATCGACTG-3'

Use a vector pSET152 as a template. 20 µL amplified reaction includes 9 µL ddH$_2$O, 2 µL 10×PCR Buffer, 1 µL DMSO, each primer (20 µM) 1 µL, 4 µL dNTP (each 2.5 mM), 1 µL Taq enzyme, and 1 µL pSET152.

PCR amplification conditions: initial 3 min denaturation at 95° C., then 1 min denaturation at 94° C., 1 min annealing at 55° C., 1 min extension at 72° C., 30 cycles in total.

After 1.5% agarose gel electrophoresis, separation of PCR products is of about 1000 bp.

Recover the 5 PCR products and transformed into E. coli BW25113/pJTU318-3 via electrotransformation. Inoculate into LB plate and grow for 12 h-16 h. Use colony-PCR and restriction enzyme digestion to verify the positive clone.

Transform the obtained replacement vector into E. coli ET12567, and conjugation with a wild Streptomyces xiamenensis spore.

After non-selective growth, apramycin-resistant exconjugates that were sensitive to thiostrepton, putatively resulting from double-crossover events, were selected, and their genotype was then confirmed by PCR with the appropriate primers.

Fifthly, after HPLC analysis, in a supernatant of a culture broth of each mutant strains of the ximB, ximC, ximD, and ximE, this benzopyran compound disappeared. An intermediate derivative compound (Xiamenmycin B) appears in the culture broth of the mutant ximA. Therefore, it is proved that this gene cluster is responsible for the biosynthesis of this benzopyran compound.

Ferment the wild and mutant strains in a shake flask with a fermentation medium. Spore suspension is inoculated respectively in the 50 ml TSB medium at 30° C., 220 rpm, for 48 h.

In the third day, inoculate them in an ISP2 medium with 100 ml and culture at 30° C., 220 rpm, for 5 days.

In the sixth day, after centrifugation, collect a supernate and then dried under water bath at 70° C. After that a residual is dissolved in 1 mL methyl alcohol and filtrated with 0.45 mm cellulose membrane. And then, samples are analyzed by HPLC with an RP-18 column (Agilent Eclipse XDB-C18; 4.6*250 mm; 5 µm).

Mobile phase composition: acetonitrile and 0.1% formic acid by gradient elution. Linear gradient elution is the concentration of acetonitrile shall be increased from 15% to 40% over 8 min, 40% to 55% over 11 min, 55% to 85% over 7 min. Then, after 4 minutes, the concentration shall be decreased to 15% and keep this balance for 3 minutes. Flow rate: 0.5 mL/min, Uv single-wave: 254 nm, wavelength scanning: 190~400 nm, interval: 2 nm, sample size: 10 µL.

FIG. 1 shows HPLC detection of fermentation products for the wild strain, the ximA mutant strain, the ximB mutant strain, the ximC mutant strain, the ximD mutant strain, the ximE mutant strain, and the Streptomyces lividans with the integration plasmid carring the xim gene cluster, and wild Streptomyces lividans, as seen in FIG. 1. FIG. 1 (A) is the HPLC for wild strain, peak A is Xiamenmycin, FIG. 1 (B) is the HPLC for the ximA mutant strain, peak B is Xiamenmycin B, FIG. 1 (C) is the HPLC for the ximB mutant strain, peak A (Xiamenmycin) disappears, FIG. 1 (D) is the HPLC for the ximC mutant strain, peak A (Xiamenmycin) disappears, FIG. 1 (E) is the HPLC for the ximD mutant strain, peak A (Xiamenmycin) disappears, FIG. 1 (F) is the HPLC for the ximE mutant strain, peak A (Xiamenmycin) disappears.

Sixthly, isolation and structural identification of Xiamenmycin B from the fermentation broth of the mutant strain of the ximA by preparative HPLC.

Ferment the mutant strains in the shake flask with the fermentation medium. Spore suspension is inoculated respectively in the 50 ml TSB medium at 30° C., 220 rpm, for 48 h. In the third day, inoculate seed culture to 200 flasks containing 100 ml ISP2 medium and culture at 30° C., 220 rpm, for 5 days. In the sixth day, after centrifugation, collect the supernate, then dried under water bath at 70° C. After that the residual is dissolved in 1 mL methyl alcohol and filtrated with 0.45 mm cellulose membrane. And then, the samples are analyzed by the HPLC with the RP-18 column (Agilent Eclipse XDB-C18; 4.6*250 mm; 5 µm). Mobile phase composition: acetonitrile and 0.1% formic acid by gradient elution. Linear gradient elution is the concentration of acetonitrile shall be increased from 15% to 40% over 8 min, 40% to 55% over 11 min, 55% to 85% over 7 min. Then, after 4 minutes, the concentration shall be decreased to 15% and keep this balance for 3 minutes. Flow rate: 0.5 mL/min, Uv single-wave: 254 nm, wavelength scanning: 190-400 nm, interval: 2 nm, sample size: 5 µL.

The Xiamenmycin B is yellow powder. By analyzing H and C atlas, a structure formula is shown as FIG. 1G. NMR data are listed as in the following tables:

¹H NMR data of the Xiamenmycin B (in DMSO-d₆)

| Site | Xiamenmycin B |
|---|---|
| 1 | — |
| 2 | — |
| 3 | 3.75, t[b] |
| 4 | 2.68, dd (7.5, 7.5) |
|   | 2.94, dd (5.5, 5.0) |
| 4a | — |
| 5 | 7.672, s |
| 6 | — |
| 7 | 7.638, d (9.0) |
| 8 | 6.777, d (8.0) |
| 8a | — |
| 9 | 1.60, m |
| 10 | 2.08, m |
| 11 | 5.098, dd (6.0, 7.5) |
| 12 | — |
| 13 | 1.552, s |
| 14 | 1.628, s |
| 15 | 1.176, s |
| 1' | — |
| 2' | — |
| 3' | — |
| 4' | — |
| 5' | — |
| 6' | — |

¹³C NMR data of the Xiamenmycin B

| Position | Xiamenmycin B |
|---|---|
| 1 | — |
| 2 | 79.61 |
| 3 | 65.70 |
| 4 | 30.60 |
| 4a | 120.35 |
| 5 | 130.81 |
| 6 | 124.25 |
| 7 | 128.80 |
| 8 | 116.41 |
| 8a | 156.87 |
| 9 | 37.45 |
| 10 | 21.12 |
| 11 | 122.25 |
| 12 | 131.69 |
| 13 | 17.41 |
| 14 | 25.41 |
| 15 | 18.40 |
| 1' | 167.08 |
| 2' | — |
| 3' | — |
| 4' | — |
| 5' | — |
| 6' | — |

Example 2, Functional Verification of the Whole Gene Cluster as Shown as in SEQ ID NO. 1

This embodiment adopts a method that verification of the whole gene cluster's function via heterologous expression of the gene cluster in the *Streptomyces lividans*. By cloning the whole gene cluster as shown in SEQ ID NO. 1 into the vector pSET152, a new vector pLMO09404 is constructed. After the vector pLMO09404 was integrated into the *Streptomyces lividans*, existence of the Xiamenmycin B is able to be detected in the fermentation broth.

Firstly, design primer using p9A11 as a template;

Forward primer:
(SEQ ID NO. 16)
5'-GCTCTAGACGGCTGGAGTGTAGCGAGTCTGGAATG-3';

Reverse primer:
(SEQ ID NO. 17)
5'-GGAATTCCCCGGACGTGGGAGCGATAGGG-3'.

This PCR product is about 7.5 kb, covering the whole gene cluster. Use high success ratio PCR enzyme KOD FX.

PCR system: 2×PCR Buffer 25 μL; 2 mM dNTP 10 μL; primer 10 pmol/μL, each for 1.5 μL, template 150 ng/μL 1 μL, KOD FX 1 μL, water 10 μL.

PCR amplification was carried out using the following procedure: denaturation at 94° C. for 2 min; 40 cycles of 98° C. for 10 sec, 68° C. for 8 min. Preserve the PCR product in 4° C.

PCR production was separated by electrophoresis with the 1% agarose gel, and recovered 7.5 Kb DNA fragment, then ligated to pMD18-T.

The ligation mix consisted of the follows: the insertion fragment 2 μL (158 ng/μL), the vector 3 μL (50 ng/μL), solution I 5 μL, 16° C., 15 h.

The ligation product was transformed to *E. coli* DH5α. The positive clone was identified by colony PCR and restriction enzyme digestion. The inserted PCR fragment was cutted out as an XbaI and HindIII fragment. Recovery 7.5 Kb DNA fragment and cloned into pSET152 that already digested by the XbaI and the HindIII. Ligation mix consists of: insertion fragment 5 μL (99 ng/μL, vector 1 μL (50 ng/μL), solution I 6 μL, 16° C., 15 h. After ligation, transform *E. coli* DH5α. The positive clone was verified by colony-PCR and restriction enzyme digestion (XbaI and HindIII).

Secondly, introduce the above-mentioned plasmid into *E. coli* ET12567, and conjugate with wild *Streptomyces lividans* spore. Screen exconjugates by using PCR to get the positive clone.

Figure 1A:
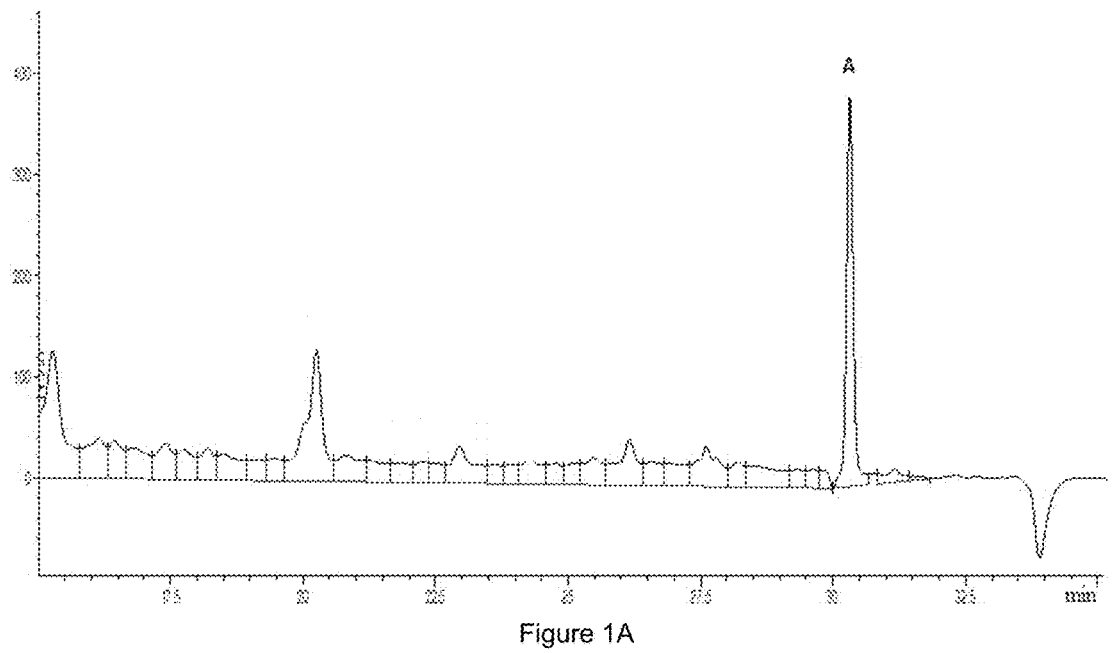
FIG. 1A is the high performance liquid chromatography (HPLC) of wild strain's fermentation products.
Figure 1B:
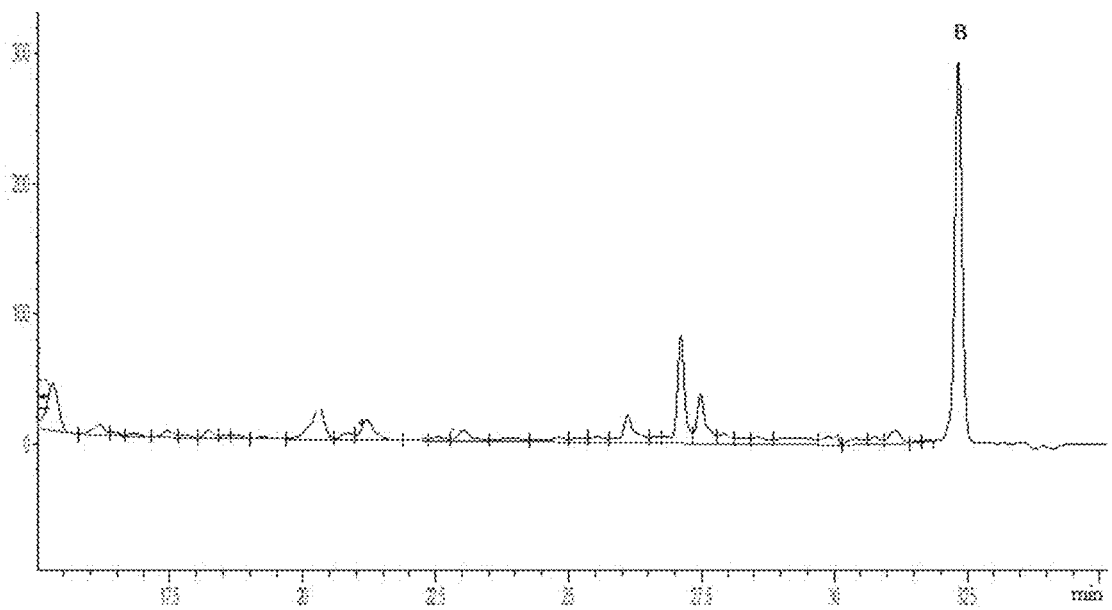
FIG. 1B is the HPLC profile of fermentation products of ximA mutant.
Figure 1C:
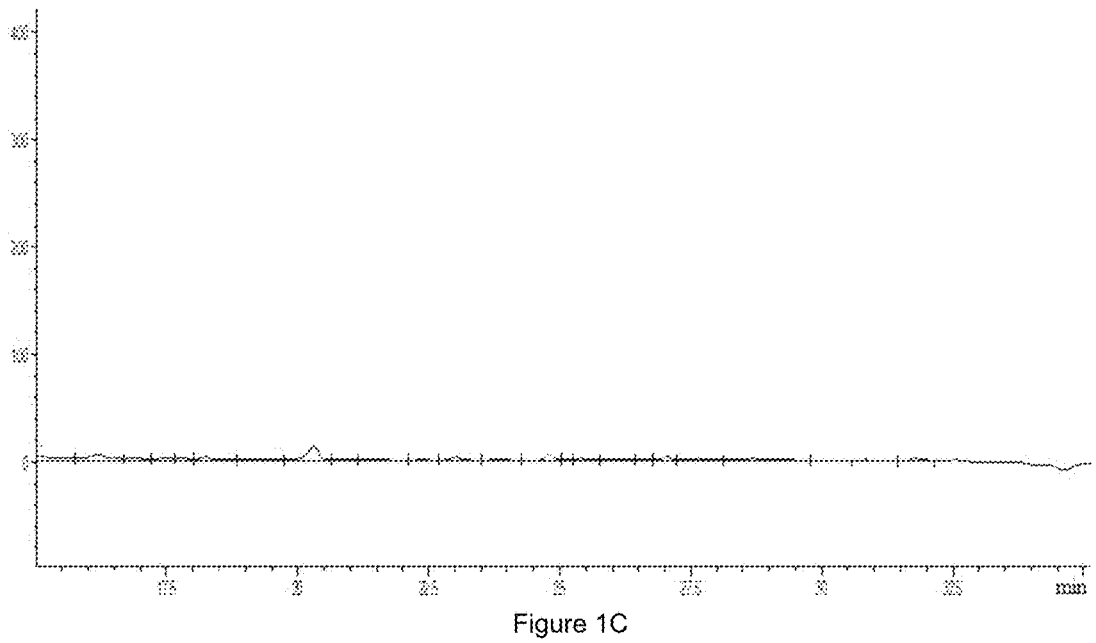
FIG. 1C is the HPLC profile of fermentation products of ximB mutant.
Figure 1D:
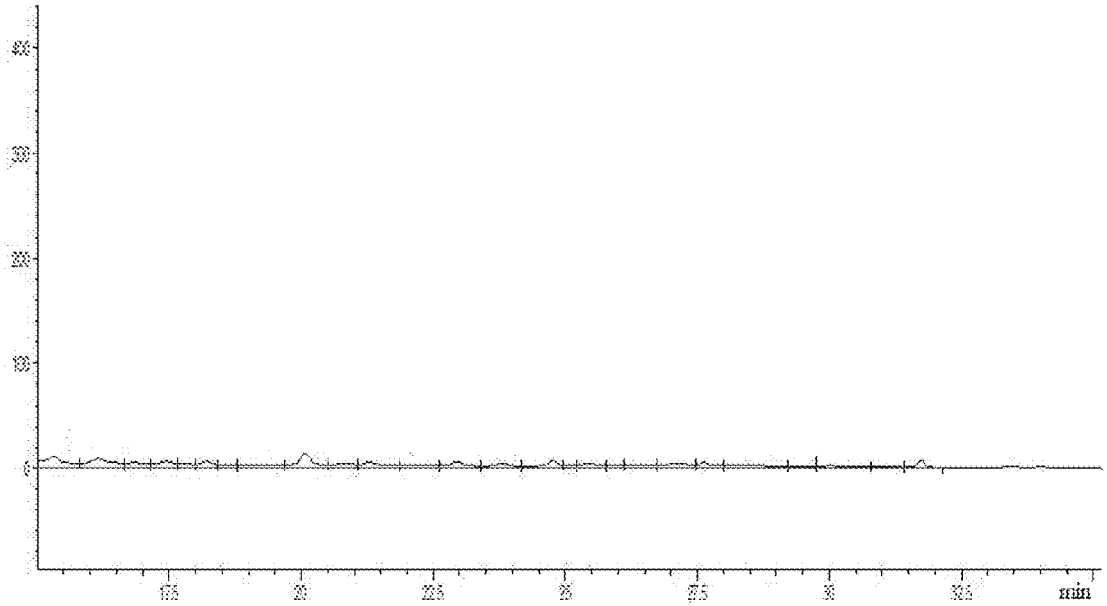
FIG. 1D is the HPLC profile of fermentation products of ximC mutant.
Figure 1E:
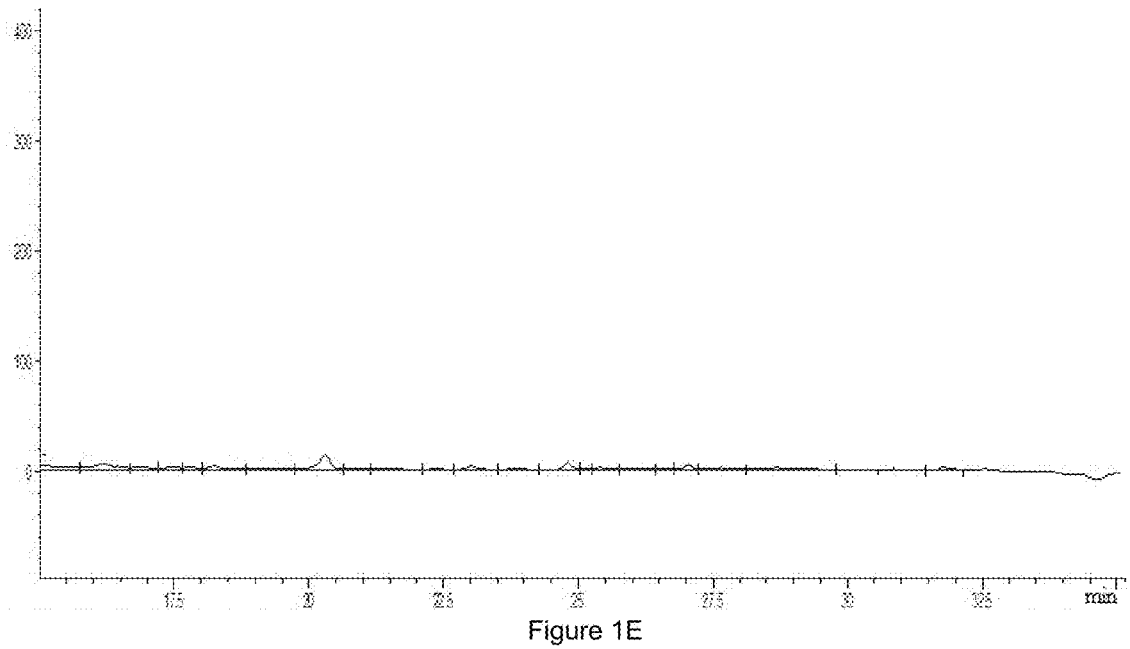
FIG. 1E is the HPLC profile of fermentation products of the ximD mutant.
Figure 1F:
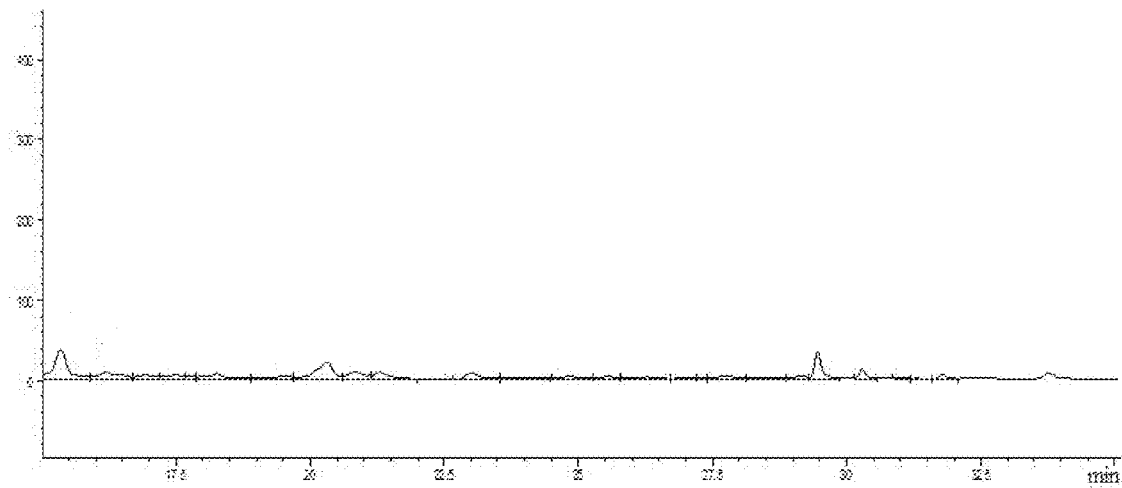
FIG. 1F is the HPLC profile of fermentation products of ximE mutant strain.
Figure 1G:
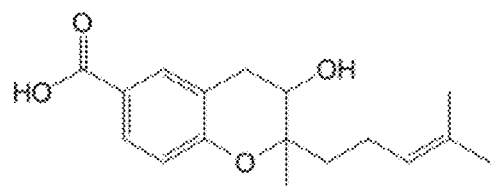
FIG. 1G is the structural formula of Xiamenmysin B.
Figure 2:
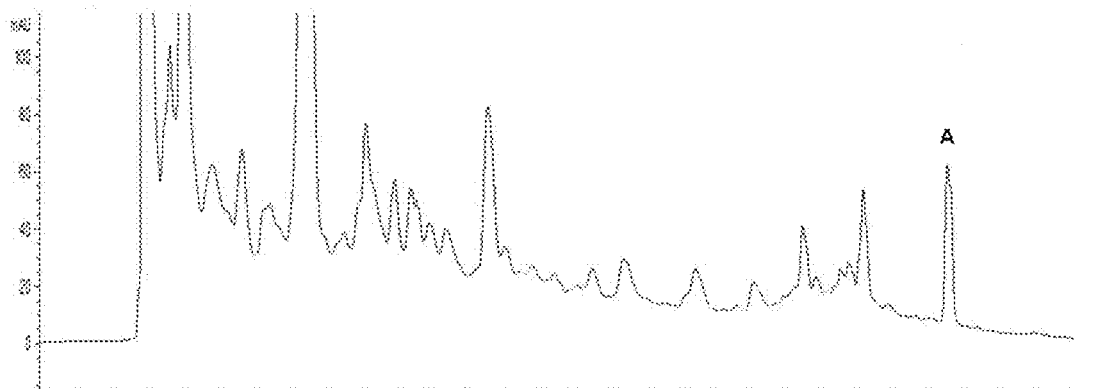
FIG. 2: the heterologous expression of Xiamenmycin biosynthesis gene cluster in *Streptomyces lividans*.
Figure 2:
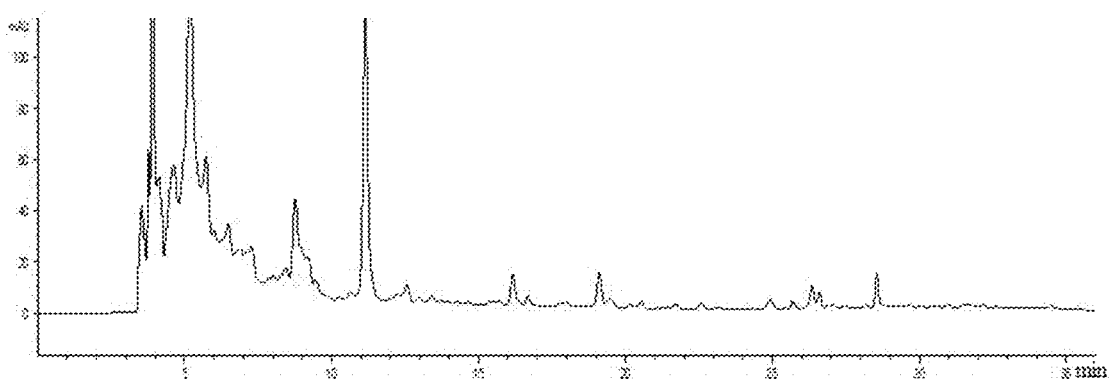

Thirdly, after the fermentation of the above mentioned strains, the Xiamenmycin was detected by the HPLC. The heterologous expression of the Xiamenmycin biosynthesis gene cluster in the *Streptomyces lividans* is shown as in FIG. 2. FIG. 2 (A) is a HPLC profile after the vector pLMO09404 is inserted into the wild *Streptomyces lividans*, and the Peak A means the Xiamenmycin. FIG. 2 (B) is the HPLC profile of the wild strain of the *Streptomyces lividans*, and there is no peak of the Xiamenmycin detected. Therefore, biosynthesis of the Xiamenmycin using the whole gene cluster, as show in the SEQ ID NO.1, has been proved in this embodiment.

Example 3 Site-Directed Mutagenesis of rpsL Gene in the *Streptomyces Xiamenensis* is Able to Raise Production of the Xiamenmycin Step 1: Design primers based on a sequence of rpsL that encode ribosome S12 protein in *Streptomyces xiamenensis* genome. And the gene is subjected to the site-directed mutagenesis using PCR to generate point mutations in the rpsL gene, namely, K43R, K88E and L90K respectively.

| | | (SEQ ID NO. 18) |
|---|---|---|
| K43R-F: | CACCACCCCGAGGAAGCCGAACTC | |
| K43R-R: | GAGTTCGGCTTCCTCGGGGTGGTG | (SEQ ID NO. 19) |
| K88E-F: | GGCCGTGTGGAGGACCTGCCGGGTG | (SEQ ID NO. 20) |
| K88E-R: | CACCCGGCAGGTCCTCCACACGGCC | (SEQ ID NO. 21) |
| L90K-F: | GTGTGAAGGACAAGCCGGGTGTCCG | (SEQ ID NO. 22) |
| L90K-R: | CGGACACCCGGCTTGTCCTTCACAC | (SEQ ID NO. 23) |

Step 2, NdeI and EcoRI restriction sites are used to clone the mutant rpsL gene into the corresponding sites of pIB139. After PCR amplification, the mutation rpsL gene was obtained and cloned into vector pMD-18, to generate plasmid p820/K43R, p822/K88E, and p827/L90K.

After restriction enzyme digestion with NdeI and EcoRV, recover the 391 by DNA fragment, then ligated with the fragment of 5.7 kb NdeI/EcoRV DNA fragment recovered from pIB139 to generate a plasmid 827/pIB139(L90K).

Step 3, transform the mutant rpsL gene into E. coli ET12567::pUZ8002, and used two parental E. coli-Streptomyces conjugations, and then the mutant rpsL gene was transformed into Streptomyces xiamenensis. Enzyme digestion that used to confirm the integration was shown in FIG. 3. Results are in accordance with the expectation.

These mutant strains, namely, 3 antibiotic-resistant mutant strains from the Streptomyces xiamenensis has been preserved in the China General Microbiological Culture Collection Center (CGMCC), in 29 Dec. 2011. Address: No. 3, No. 1 Yard, West Beicheng Road, Chaoyang District, Peking, Institute of Microbiology of Chinese academy of Sciences, Culture Preservation No.: CGMCC No. 5674, CGMCC No. 5675 and CGMCC No. 5676, respectively carring 3 mutant rpsL genes as, K88E, L90K and K43R.

Step 4, after fermentation of these mutants, detect the Xiamenmycin by the HPLC. The Xiamenmycin production of the mutants is shown as in FIG. 4. The results show that the Xiamenmycin (peak A) production of mutants M5, M6, and M7 are greatly improved, and it is about 10-20 times of the wild type strain; besides a yield of other compound as peak B, C, D, E, and F are improved greatly as well.

In conclusion, the present invention provides microbial strains that are able to be used in the biosynthesis of the benzopyran compounds by fermentation, which includes the Streptomyces xiamenensis, its mutants and the genetically modified strains that carring the Xiamenmycin biosynthesis gene cluster, and the mutants are able to be applied in the industrial production.

The preferred embodiments of the invention are described above. We have to understand that the invention is not limited to the above specific methods of implementation and technicians in the same field can do all kinds of transformations or modifications within the claim which will not affect the essential points of the invention.

What is claimed is:

1. A method to produce Xiamenmycin, comprising steps of: selecting genetic engineered microbial strains caning the Xiamenmycin biosynthesis gene cluster with a nucleotide sequence showed as an entire full length of SEQ ID NO.1 and with a whole length of 5189 bp, then fermenting the genetic engineered microbial strains in a fermentation medium to produce the Xiamenmycin.

* * * * *